United States Patent [19]

Little

[11] 4,214,594
[45] Jul. 29, 1980

[54] TEMPORARY PACEMAKER LEAD APPARATUS

[75] Inventor: Richard L. Little, Minneapolis, Minn.

[73] Assignee: Daig Corporation, Minnetonka, Minn.

[21] Appl. No.: 949,088

[22] Filed: Oct. 6, 1978

[51] Int. Cl.³ .............................................. A61N 1/04
[52] U.S. Cl. .................................. 128/786; 128/419 P
[58] Field of Search ................... 128/419 P, 784, 785, 128/786

[56] References Cited

U.S. PATENT DOCUMENTS

| | | | |
|---|---|---|---|
| 3,485,247 | 12/1969 | Ackerman | 128/786 |
| 3,533,403 | 10/1970 | Woodson | 128/419 P |
| 3,769,984 | 11/1973 | Muench | 128/419 P |

*Primary Examiner*—William E. Kamm
*Attorney, Agent, or Firm*—Clayton R. Johnson

[57] ABSTRACT

Temporary pacemaker lead apparatus that includes a bifurcated lead assembly having a first and a second electric conductor pin connectable to terminals of an external pulse generator, a ring electrode more closely adjacent to the pins than the tip electrode, a first electric conductor having a first end electrically connected to the first pin, an intermediate portion extending through a tubular member and a second end electrically connected to the tip electrode, a second electric conductor connected to the second pin, an intermediate portion extended through the above mentioned tubular member and a second end connected to the ring electrode, a junction member having the first and second conductor intermediate portions extended therethrough, the junction member having means which connects to the head portion of a lead introducer cannula head portion for storing the cannula after the cannula has been used in extending the electrode end portion of the lead assembly into a body vessel, for example a vein. A needle is extended through the cannula for initially puncturing the body vessel.

4 Claims, 6 Drawing Figures

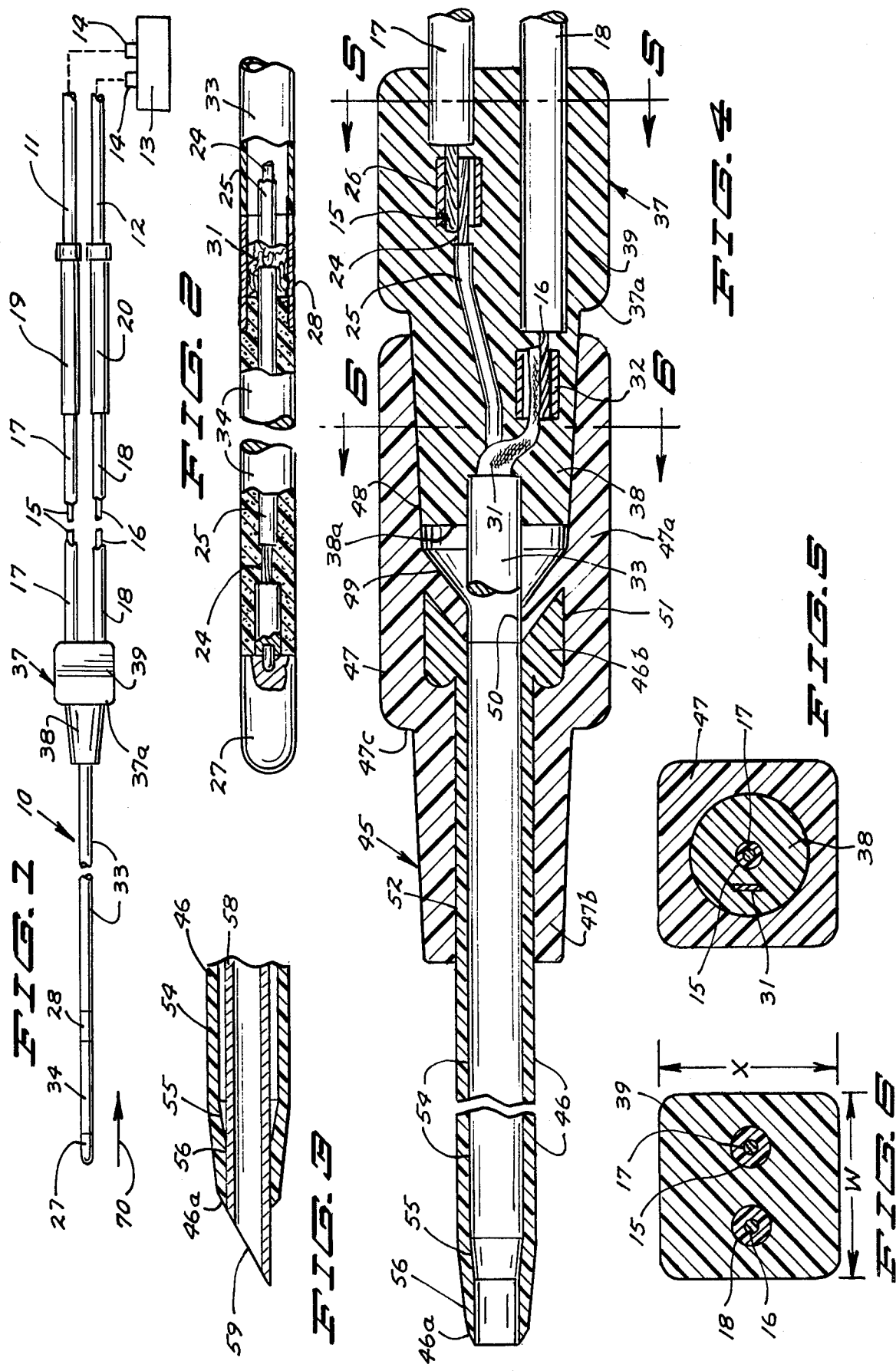

TEMPORARY PACEMAKER LEAD APPARATUS

BACKGROUND OF THE INVENTION

Temporary pacemaker lead apparatus for having its electrode end portion inserted through a cannula and fed into a vessel of the body such as a vein.

In the prior art, one technique for inserting the electrode end of a temporary lead assembly into a vessel is the use of a procedure commonly called a "cut down." This technique involves cutting through the skin, exposing approximately one-half inch length of the vessel and cutting a slit in the vessel. The electrode end of the lead assembly is then inserted through the slit in the vessel and advanced into the vessel. This procedure is messy, time consuming (an important factor in emergency situations) and requires a sterile environment.

A second technique requires the use of a two part lead, one part of which is bifilar for connecting to an external pulse generator, the other part of which is unifilar for inserting into a vessel. In this technique, a plastic cannula is placed over a hypodermic needle and the needle is used to puncture and enter a vessel. The needle is withdrawn and the electrode end of the unifilar portion of the lead is inserted through the vessel. The cannula is then withdrawn and slid along the entire length of the unifilar segment of the lead and slid off the end opposite the electrode end and discarded. The opposite end of the unifilar segment is then physically and electrically connected to the bifilar segment via built in electro/mechanical connector. The disadvantages of this technique are: the difficulty of making the electro/mechanical connection of the bifilar and unifilar segments under the usual conditions in which the physician's gloves and the lead itself are covered with blood, body fluids and aseptic liquids; the relatively unreliable electro/mechanical connection between the unifilar and bifilar segments; the possibility of the patient tampering with the connection; and it is time consuming.

In order to overcome problems such as the above, this invention has been made.

SUMMARY OF THE INVENTION

A bifuracted lead assembly having electrical conductors electrically connecting bifurcated pins to ring and tip electrodes that are remote from the pins and a junction member through which the conductors extend, and a cannula for facilitating inserting the electrode end portion into a vessel, the junction member having a portion connectable to the head end base portion of the cannula for releasably retaining the cannula in a position remote from the vessel after the cannula has been used for initially inserting the lead assembly electrode end portion into the vessel.

One of the objects of this invention is to provide a temporary pacemaker lead assembly and a cannula with new and novel means for storing the cannula after the lead assembly has been extended into a vessel and prior to the removal of the lead assembly from the vessel. Another object of the invention is to provide a temporary pacemaker lead assembly junction member and a cannula head end portion with new and novel portions that corporate to retain the cannula in abutting relationship with the junction member after the cannula has been used to insert the electrode end portion into the vessel.

BRIEF DESCRIPTION OF THE DRAWINGS

FIG. 1 is a diagrammatic view of a pulse generator and a plan view of a temporary pacemaker lead assembly of this invention, axially intermediate portions of the assembly being broken away;

FIG. 2 is an enlarged fragmentary view of the electrode end portion of the lead assembly, various structural portions being shown in cross section;

FIG. 3 is an enlarged cross sectional view of the end portions of a cannula and hypodermic needle that are insertable into a vessel to show the relative positions thereof when the head end portion of the needle is seated in the head end portion of the cannula;

FIG. 4 is an enlarged longitudinal cross sectional view of the cannula and the junction member of the lead assembly of this invention with the cannula being seated on the junction member in a storage position, an axially intermediate part of the tubular end of the cannula that extends outwardly of the head end being broken away;

FIG. 5 is a transverse cross sectional view generally taken along the line and in the direction of the arrows 5—5 of FIG. 4 to further illustrate the construction of the head end portion of the junction member; and FIG. 6 is a transverse cross sectional view of substantially the same scale as that of FIG. 5 to illustrate the seating of the cannula head end portion on the junction member, said view being generally taken along the line and in the direction of the arrows 6—6 of FIG. 4.

Referring now to FIG. 1, the bipolar, temporary pacemaker lead assembly of this invention, generally designated 10, includes a connector pin 11 electrically connected to one end of a wire 15 having electric insulation 17 thereon and a connector pin 12 electrically connected to one end of a wire 16 having electric insulation 18 thereon. The adjacent end portions of pin 11 and insulation 17 extend into an electrical insulating sleeve 19 while the adjacent end portions of pin 12 and insulation 18 extend into an electrical insulating sleeve 20. The pins are provided for being electrically connected with a pair of terminals 14 of a pulse generator 13 that provides pulses for maintaining a desired rate of heart beat.

A crimped connector 26 electrically connects the end of wire 15 remote from pin 11 to the one end of wire 24 of an electric conductor, the wire extending through a ring electrode 28 and having an opposite end electrically connected to a tip electrode 27. Electric insulation 25 is provided on wire 24 from adjacent connector 26 to the tip electrode. A crimped connector 32 electrically connects the end of wire 16 remote from pin 12 to end of a braided electrical conductor 31, the opposite end of conductor 31 being electrically connected to the ring electrode 28.

The electrical conductor 24, 25 and the braided conductor 31 extend through a plastic tubular member 33, tubular member 33 extending from adjacent connector 32 to the ring electrode. A plastic molded member 34 surrounds electrical conductor 24, 25, and extends from the ring electrode to the tip electrode. Members 31, 24, 25, and 33 are of sufficient flexibility so that they can be inserted through a body vessel, for example a vein, to position the tip electrode in an organ, for example the heart.

The crimped connectors, the adjacent end portions of the electrical conductors to which they are respectively connected and the adjacent end portions of tubular member 33 are embedded in a molded junction member, generally designated 37. The electrical conductors are bifurcated from the junction member to the pins. Advantageously items 33, 17 and 18 are made of low density polyethylene. The junction member includes a generally rectangular block end portion 39 and a frusto conical cannula storage portion 38 having its major base end integrally joined to the block end portion. The frusto conical portion is more remote from the pins 11, 12 than the block portion 39. Thus along the length of the lead assembly, the minor base end 38a is located more closely adjacent the ring electrode than the remainder of the junction member. Members 31, 33, 24, 25 pass through the minor base end 38a. The transverse major diameter of the frusto conical portion 38 is less than the transverse width and height dimensions W and X of the block portion whereby a peripheral shoulder 37a is formed at the juncture of portions 38, 39. Preferably the frusto conical portion is of a Luer Taper.

To be used in conjunction with the lead assembly 10, there is provided a lead introducer cannula, generally designated 45. The cannula includes an axially elongated tube 46 and a head end portion 47 that is of a substantially larger cross section, the enlarged head end portion 46b of the tube being embedded in the rectanular block portion 47a of the head end portion 47. The tube includes a circular reduced diameter bore portion 56 that opens at one end through the tapered annular end portion 46a and at the other end to the minor base end of frusto conical bore portion 55. The major base end of bore portion 55 opens to one end of the axially elongated circular bore portion 54 which opens outwardly through the tube head end portion 46b.

The head end portion 47 includes frusto conical end portion 47b having a major base end integrally joined to one end of a generally rectangular block portion 47a. The transverse height and width of the block portion 47a is greater than the major base diameter of frusto conical portion 47b to provide a peripheral shoulder 47c.

A bore extends axially through the head portion 47, the bore including an axially elongated, frusto conical bore portion 48 having a major base end opening outwardly through the head portion 47a axially opposite the frusto conical portion 47b. Bore portion 48 is of substantially the same axial length as frusto conical portion 38 and of a taper to form a close friction fit with frusto conical portion 38. Advantageously both bore portion 48 and frusto conical portion are of Luer Tapers whereby when frusto conical portion 38 is pushed into bore portion 48, it is releasably locked to the junction member, i.e. relatively difficult to separate the cannula from the junction member by merely pulling them in axially opposite directions, but relatively easy to separate them if one is twisted relative the other at the same time they are being pulled in axially opposite directions.

The minor base end of bore portion 48 opens to the major base end of frusto conical bore portion 49 which is of a much shorter axial length than that of bore portion 48 and of an angle of taper that is much larger than that of bore portion 48. The minor base end of bore portion 49 opens to one end of the circular cylindrical bore portion 50 which is of substantially the same diameter as the diameter of bore portion 54. Bore portion 50 opens to bore portion 51 which is of a size and shape to receive the tube head portion 46b. Bore portion 51 opens to the circular cylinder bore portion 52 which extends through the frusto conical portion and is of a diameter to have the part of the tube adjacent head portion 46b extend therethrough. Tube bore portion 54 is of substantially the same diameter as bore portion 50 and opens directly thereto.

To facilitate puncturing the body vessel, for example a vein in the arm or leg, there is provided a hypodermic needle 58, the sharpened end 59 of the needle advantageously being of substantially the same taper as the tube tapered end surface 46a. The needle point end portion of the needle is of an outer diameter to form a close fit with bore portion 56 (see FIG. 3) while the head end portion (not shown) of the needle advantageously has a frusto conical bore portion that forms a close friction fit with frusto conical portion 47b when the lead introducer cannula and needle are in relationship shown in FIG. 3 for initially puncturing the body vessel and the cannula end portion opens into the vessel.

After the vessel has been punctured to have the cannula bore portion 56 open thereinto, the needle is withdrawn with the cannula left in place. Thereafter the lead assembly electrode tip portion is pushed through the cannula bore portion 48 and thence through bore portion 56 to extend into the body vessel. After the electrode tip 27 has been pushed through the vessel to its desired location in an organ, for example the heart, the cannula is withdrawn from the vessel and moved in the direction of arrow 70 along the tubular member 33 which extends therethrough to the FIG. 4 position. The frusto conical bore portion 48 seats on the frusto conical cannula storage portion 38 of the junction member. At this time the cannula is remote from the puncture in the skin that tubular member 33 extends through, the axial length of tubular member 33 being many times greater than the axial length of the cannula. Due to the friction fit between the lead assembly portion 38 and cannula portion 47a, the cannula is retained in a storage position on the cannula until the lead assembly is withdrawn from the vessel, and is not free to slide along the length of tubular member 33. If the press fit is obtained with a Luer Taper, the cannula can be removed from the junction member (storage position of FIG. 4) by pulling and at the same time twisting the cannula to rotate on the frusto conical portion 38 to release the locking engagement between bore portion 48 and frusto conical portion 38.

What is claimed is:

1. The combination of a temporary bipolar, bifurcated lead assembly for being inserted into a body vessel for transmitting pulses from a pulse generator to a heart and a lead introducer cannula for having the lead assembly extended therethrough and into the vessel, the lead assembly including a first and a second connector pin adapted to being electrically connected to a pulse generator, a tip electrode, a ring electrode, a junction member of electrical insulating material, a first electrical conductor portion having a first end portion electrically connected to the first pin and second end portion located within the junction member, a second electric conductor portion having a first end portion electrically connected to the second pin and a second end portion located within the junction member, an elongated third electric conductor portion having a first end portion electrically connected to the first conductor portion second end portion, an intermediate portion extending through the ring electrode and a second end portion electrically connected to the tip electrode, an elongated fourth conductor portion having a first end portion electrically connected to the second conductor portion second end portion and a second end portion electrically connected to the ring electrode, the length of the third and fourth conductor portions from the junction member to the ring electrode being many times greater than the axial length of the cannula, the cannula and junction member having cooperating engaging means for selectively releasably retaining the cannula remote from the ring electrode, the cooperating means including a frusto conical junction member cannula engageable surface portion and a frusto conical peripheral cannula surface portion for forming a friction fit with the engageable surface portion to releasably retain the cannula on the junction member surface portion.

2. The combination of a temporary bipolar, bifurcated lead assembly for being inserted into a body vessel for transmitting pulses from a pulse generator to a heart and a lead introducer cannula for having the lead assembly extended therethrough and into the vessel, the lead assembly including a first and a second connector pin adapted to being electrically connected to a pulse generator, a tip electrode, a ring electrode, an elongated first electric conductor having a first end portion electrically connected to the first pin, a second end portion electrically connected to the tip electrode, and an intermediate portion, a second electric conductor having a first end portion electrically connected to the second pin, a second end portion electrically connected to the ring electrode, and an intermediate portion, a junction member joined to the conductor intermediate portions and having a cannula storage end portion that has an outer peripheral surface surrounding the conductor intermediate portions, and a tubular member surrounding the conductors from the junction member to the ring electrode, said conductors being bifurcated from the junction member to the pins, and an axially elongated lead introducer cannula having axially elongated tubular means for inserting the lead assembly into a body vessel, said tubular means having a first end portion, a second end portion and head means joined to the tubular means second end portion for engaging the cannula storage end portion a substantial distance away from the electrodes, the head means having a frusto-conical bore portion defining an inner peripheral surface of a size and shape to form a releasably locking friction fit with the storage end portion peripheral surface, the length of the conductors between the junction member and the electrodes being substantially greater than the axial length of the cannula.

3. The combination of claim 2 further characterized in that each of said surfaces have a Luer Taper.

4. The apparatus of claim 11 further characterized in that said cannular storage end portion is frusto-conical and has a major base end and that the junction member has a block portion joined to the major base end of the storage end portion, the transverse major diameter of the storage end portion being of a dimension that is less than the transverse width and height dimensions of the block portion whereby a peripheral shoulder is formed at the juncture of the storage end portion and the block portion.

* * * * *

UNITED STATES PATENT AND TRADEMARK OFFICE
CERTIFICATE OF CORRECTION

PATENT NO. : 4,214,594

DATED : July 29, 1980

INVENTOR(S) : Richard L. Little

It is certified that error appears in the above-identified patent and that said Letters Patent are hereby corrected as shown below:

Column 6, line 20, change "11" to --2--.

Signed and Sealed this

Twenty-first Day of October 1980

[SEAL]

Attest:

SIDNEY A. DIAMOND

Attesting Officer

Commissioner of Patents and Trademarks